(12) United States Patent
Koyama

(10) Patent No.: US 8,838,244 B2
(45) Date of Patent: Sep. 16, 2014

(54) CARDIAC PACEMAKER DEVICE WITH CIRCUITS FOR MONITORING RESIDUAL CAPACITY OF BATTERY

(75) Inventor: Jun Koyama, Sagamihara (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 930 days.

(21) Appl. No.: 11/798,817

(22) Filed: May 17, 2007

(65) Prior Publication Data

US 2007/0282383 A1    Dec. 6, 2007

(30) Foreign Application Priority Data

Jun. 2, 2006  (JP) ................... 2006-155300

(51) Int. Cl.
*A61N 1/02* (2006.01)
*A61N 1/378* (2006.01)
*A61N 1/375* (2006.01)

(52) U.S. Cl.
CPC ............. *A61N 1/375* (2013.01); *A61N 1/3787* (2013.01)
USPC ........................................................ 607/33

(58) Field of Classification Search
USPC ................................. 607/30, 33, 36
See application file for complete search history.

(56) References Cited

U.S. PATENT DOCUMENTS

| 4,562,841 | A | * | 1/1986 | Brockway et al. | 607/29 |
|---|---|---|---|---|---|
| 5,411,537 | A | * | 5/1995 | Munshi et al. | 607/33 |
| 5,413,593 | A | | 5/1995 | Spinelli et al. | |
| 5,591,217 | A | | 1/1997 | Barreras | |
| 5,769,873 | A | * | 6/1998 | Zadeh | 607/29 |
| 5,769,877 | A | | 6/1998 | Barreras, Sr. | |
| 5,807,397 | A | * | 9/1998 | Barreras | 607/61 |
| 5,959,436 | A | | 9/1999 | Takashina et al. | |
| 6,654,638 | B1 | | 11/2003 | Sweeney | |
| 6,805,998 | B2 | | 10/2004 | Jenson et al. | |

(Continued)

FOREIGN PATENT DOCUMENTS

| CN | 1201287 | 12/1998 |
|---|---|---|
| JP | 04-071952 | 6/1992 |

(Continued)

OTHER PUBLICATIONS

Search Report (Application No. 07010161.3) dated Sep. 23, 2008.

(Continued)

*Primary Examiner* — Brian T Gedeon
(74) *Attorney, Agent, or Firm* — Eric J. Robinson; Robinson Intellectual Property Law Office, P.C.

(57) ABSTRACT

It is necessary to periodically replace a cell of an implantable-type cardiac pacemaker device, which causes suffering to a patient as often as a cell is replaced. Thus, it is an object of the present invention to dispense with cell replacement of the cardiac pacemaker device. A cardiac pacemaker device of the present invention has an antenna and a battery built-in, and an electric power is transmitted to the built-in antenna from outside a body by an electromagnetic wave to store the electric power in the battery. With the use of the electric power stored in the battery, a main body of the pacemaker device can operate. If necessary, the electric power can be supplied wirelessly from outside and a surgery for exchanging a cell becomes unnecessary; therefore, a patient's suffering can be relieved.

11 Claims, 16 Drawing Sheets

(56) References Cited

U.S. PATENT DOCUMENTS

| | | |
|---|---|---|
| 6,924,164 B2 | 8/2005 | Jenson |
| 6,931,283 B1 * | 8/2005 | Magnusson ............... 607/36 |
| 6,962,613 B2 | 11/2005 | Jenson |
| 6,986,965 B2 | 1/2006 | Jenson et al. |
| 7,003,350 B2 | 2/2006 | Denker et al. |
| 7,058,451 B2 * | 6/2006 | Obel et al. ............... 607/27 |
| 7,131,189 B2 | 11/2006 | Jenson |
| 7,144,655 B2 | 12/2006 | Jenson et al. |
| 7,157,187 B2 | 1/2007 | Jenson |
| 7,194,801 B2 | 3/2007 | Jenson et al. |
| 7,389,580 B2 | 6/2008 | Jenson et al. |
| 7,433,655 B2 | 10/2008 | Jacobs et al. |
| 7,877,120 B2 | 1/2011 | Jacobs et al. |
| 2001/0032666 A1 | 10/2001 | Jenson et al. |
| 2001/0033952 A1 | 10/2001 | Jenson et al. |
| 2002/0000034 A1 | 1/2002 | Jenson |
| 2002/0001746 A1 | 1/2002 | Jenson |
| 2002/0001747 A1 | 1/2002 | Jenson et al. |
| 2002/0004167 A1 | 1/2002 | Jenson et al. |
| 2002/0037756 A1 | 3/2002 | Jacobs et al. |
| 2004/0185310 A1 | 9/2004 | Jenson et al. |
| 2004/0185667 A1 | 9/2004 | Jenson |
| 2004/0220667 A1 | 11/2004 | Gelfandbein et al. |
| 2005/0045223 A1 | 3/2005 | Jenson et al. |
| 2005/0189139 A1 | 9/2005 | Stole |
| 2006/0019157 A1 | 1/2006 | Jenson |
| 2006/0021214 A1 | 2/2006 | Jenson et al. |
| 2006/0063074 A1 | 3/2006 | Jenson et al. |
| 2006/0074449 A1 | 4/2006 | Denker et al. |
| 2007/0087230 A1 | 4/2007 | Jenson et al. |
| 2007/0243459 A1 | 10/2007 | Jenson et al. |
| 2009/0068556 A1 | 3/2009 | Jecobs et al. |
| 2010/0021816 A1 | 1/2010 | Stole |
| 2011/0097609 A1 | 4/2011 | Jenson et al. |

FOREIGN PATENT DOCUMENTS

| | | |
|---|---|---|
| JP | 05-317433 | 12/1993 |
| JP | 06-079005 | 3/1994 |
| JP | 0 665 032 | 8/1995 |
| JP | 07-213630 | 8/1995 |
| JP | 07-299150 | 11/1995 |
| JP | 10-258129 A | 9/1998 |
| JP | 2002-315209 | 10/2002 |
| JP | 2003-310744 A | 11/2003 |
| WO | WO-01/73957 | 10/2001 |
| WO | WO 01/76687 | 10/2001 |
| WO | WO 2004/071338 | 8/2004 |
| WO | WO-2005/042083 | 5/2005 |
| WO | WO-2007/019207 | 2/2007 |

OTHER PUBLICATIONS

Chinese Office Action (Application No. 200710108219.3) Dated Nov. 23, 2010.

European Search Report (Application No. 11002108.6) Dated Aug. 5, 2011.

Chinese Office Action (Application No. 200710108219.3) Dated May 27, 2013.

* cited by examiner

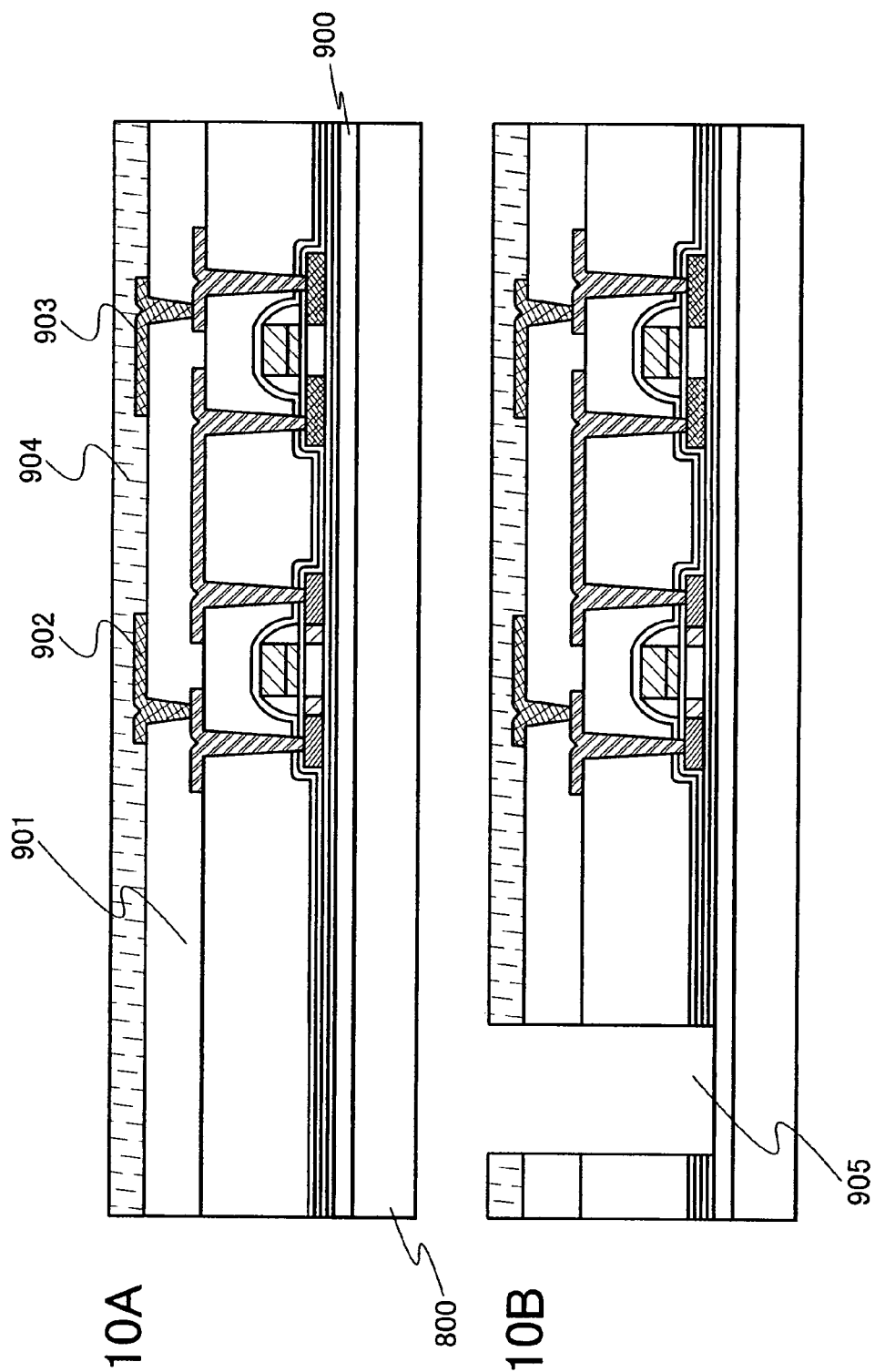

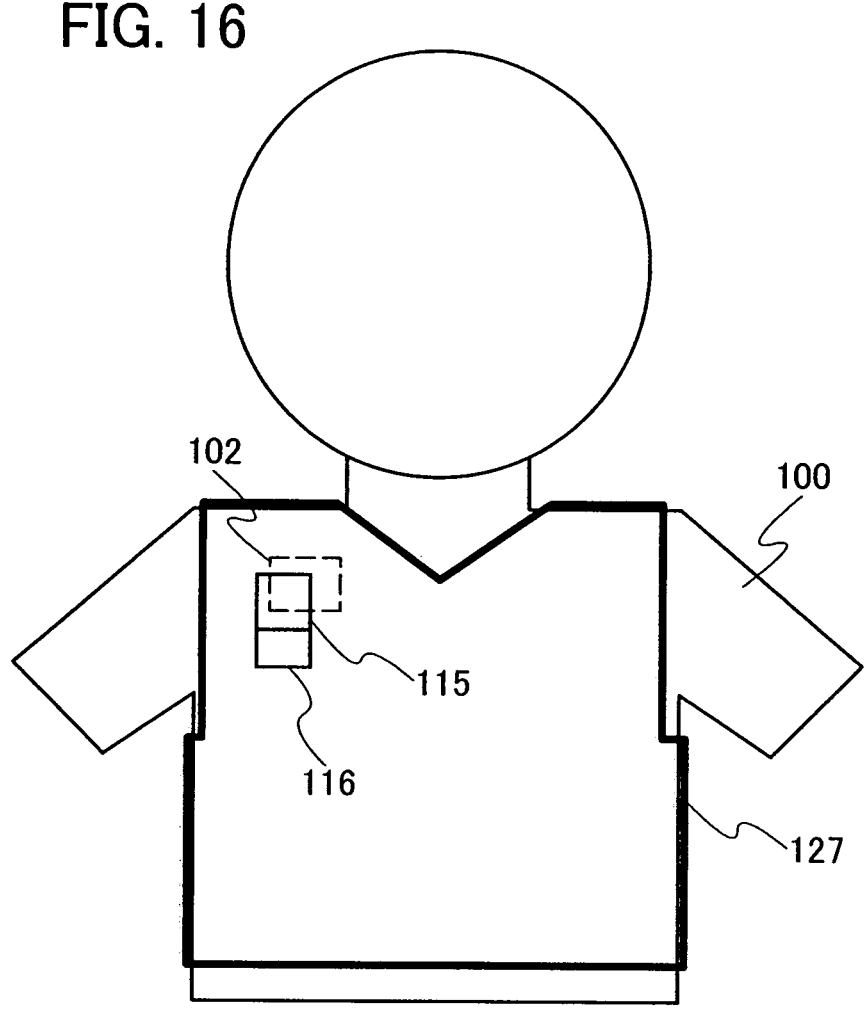

CARDIAC PACEMAKER DEVICE WITH CIRCUITS FOR MONITORING RESIDUAL CAPACITY OF BATTERY

BACKGROUND OF THE INVENTION

1. Field of the Invention

The present invention relates to a cardiac pacemaker device and particularly to a cardiac pacemaker device, which is an implantable type, capable of wirelessly receiving an electric power from outside a patient's body.

2. Description of the Related Art

A cardiac pacemaker device is a device for periodically delivering an electroshock to a cardiac patient's heart so as to operate the heart normally. As for the cardiac pacemaker device, there is an extracorporeal type that gives an electric signal from outside a cardiac patient's body and an implantable type that implants the device into a cardiac patient (for example, see Patent Document: Japanese Published Patent Application No. H7-213630).

As shown in FIG. 2, an implantable-type cardiac pacemaker device 203 is implanted into a skin which is several centimeters from a patient's shoulder 201. The cardiac pacemaker device 203 and a heart 202 are connected by wirings 204 and 205 for detecting electrocardiograms and a wiring 206 for transmitting an electric signal from the pacemaker device to the heart. The cardiac pacemaker device 203 detects electrocardiograms of the heart 202, and an electroshock is periodically delivered to the heart 202 through the wiring 206 in a case of an irregular heartbeat.

FIG. 3 shows a block diagram of the conventional cardiac pacemaker device. The cardiac pacemaker device 203 includes an atrium detection amplifier circuit 301, a chamber detection amplifier circuit 302, a controller circuit 303, a pulse generation circuit 304, and a cell 305. The atrium detection amplifier circuit 301 amplifies electrocardiograms of an atrium of the heart 202 through the wiring 204. The chamber detection amplifier circuit 302 amplifies electrocardiograms of a chamber of the heart 202 through the wiring 205. A signal amplified by these amplifier circuits is inputted into the controller circuit 303. The controller circuit 303 calculates a pulse cycle of the heart 202 to determine whether there is an irregular heartbeat. In a case of an irregular heartbeat, a signal is outputted so that the controller circuit 303 outputs a heart stimulus pulse to the pulse generation circuit 304. Based on the signal, the pulse generation circuit 304 supplies an electric signal to the heart 202 through the wiring 206. Here, the cell 305 supplies an electric power to the atrium detection amplifier circuit 301, the chamber detection amplifier circuit 302, the controller circuit 303, and the pulse generation circuit 304.

SUMMARY OF THE INVENTION

The conventional implantable-type cardiac pacemaker device described above has been had the following problem. For example, the power supply of the conventional implantable-type cardiac pacemaker device is obtained by a cell. Therefore, when the cell is died and the voltage is decreased, it is necessary to replace the cell. In order to replace the cell in a case of the conventional implantable-type cardiac pacemaker device, it is necessary to take out the cardiac pacemaker device from a patient's body. In addition, it is necessary to reimplant the cardiac pacemaker device into the patient's body after the cell is replaced. Therefore, the patient needs to periodically undergo surgery for exchanging the cell, which causes physical suffering to the patient.

It is an object of the present invention to free a patient using the cardiac pacemaker device from replacement of a cell of such a cardiac pacemaker device or reduce replacement frequency thereof, and to relieve physical suffering of a patient.

An abstract of the present invention is a cardiac pacemaker device having a battery that can be charged without contact with the utilization of an electromagnetic wave and an electric circuit that operates through supply of an electric power from the battery, particularly an implantable-type cardiac pacemaker device.

The electric circuit of the pacemaker device according to the present invention can include a charge control circuit for controlling a switching circuit depending on the charge situations of a constant current source, the switching circuit, and a battery. In addition, a residual amount detection circuit for detecting the residual amount of the battery and a modulation circuit for modulating the output of the residual amount detection circuit may be provided in some cases. By making the electromagnetic wave which is supplied from an external device to supply an electric power to the battery to a modulated wave, a structure where information of the residual amount detection circuit is transmitted to an extracorporeal control device from the modulation circuit can also be included in the electric circuit in addition to a structure where the buttery is supplied with an electric power.

At least part of the electric circuit of the pacemaker device according to the present invention is preferably composed of a thin film transistor. In addition, most of a chassis including the battery and the electric circuit is preferably formed of an insulator, and much preferably, an exterior face of the chassis is covered with a diamond-like-carbon (DLC).

As for the structure, the chassis is preferably formed of a resin material, and most of the chassis including the battery and the electric circuit is preferably formed of an insulator. In addition, the surface of the chassis is preferably covered with a diamond-like-carbon (DLC).

The pacemaker device of the present invention can obtain an electric power from outside a patient's body with the utilization of an electromagnetic wave. Consequently, it is possible to rid replacement or reduce replacement frequency of a cell which is the problem of the conventional cardiac pacemaker device. In other words, since the pacemaker device can percutaneously be provided with an electric power in a noninvasive manner, the patient can be relieved from the burden.

BRIEF DESCRIPTION OF DRAWINGS

FIGS. 10A and 10B are each a cross-sectional view of a TFT;

FIG. 16 is a view showing an example where a transmitter is incorporated into wearing clothes.

DETAILED DESCRIPTION OF THE INVENTION

Embodiment Mode

Figure 1:
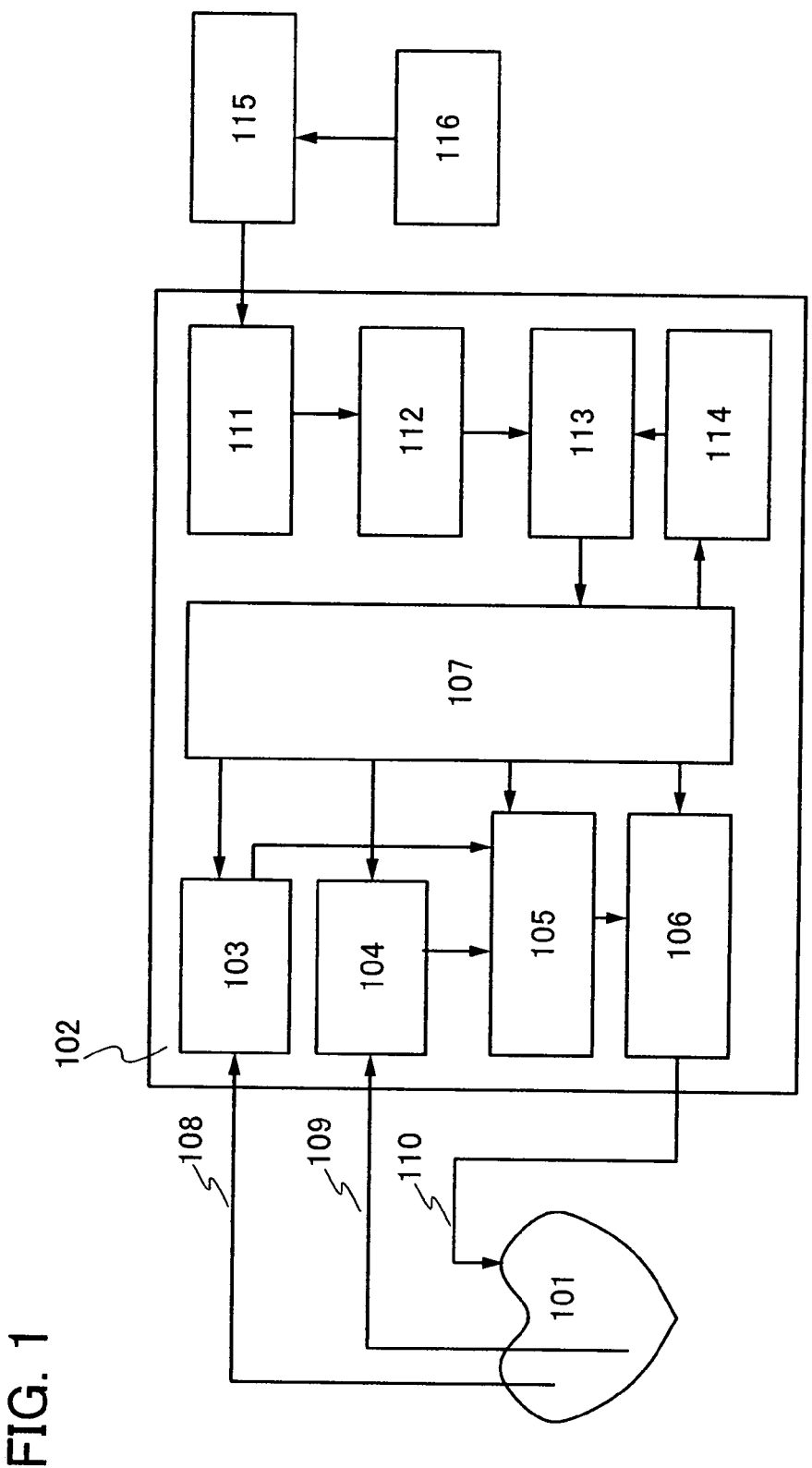
FIG. 1 is a block diagram of a cardiac pacemaker device of the present invention.
Figure 2:
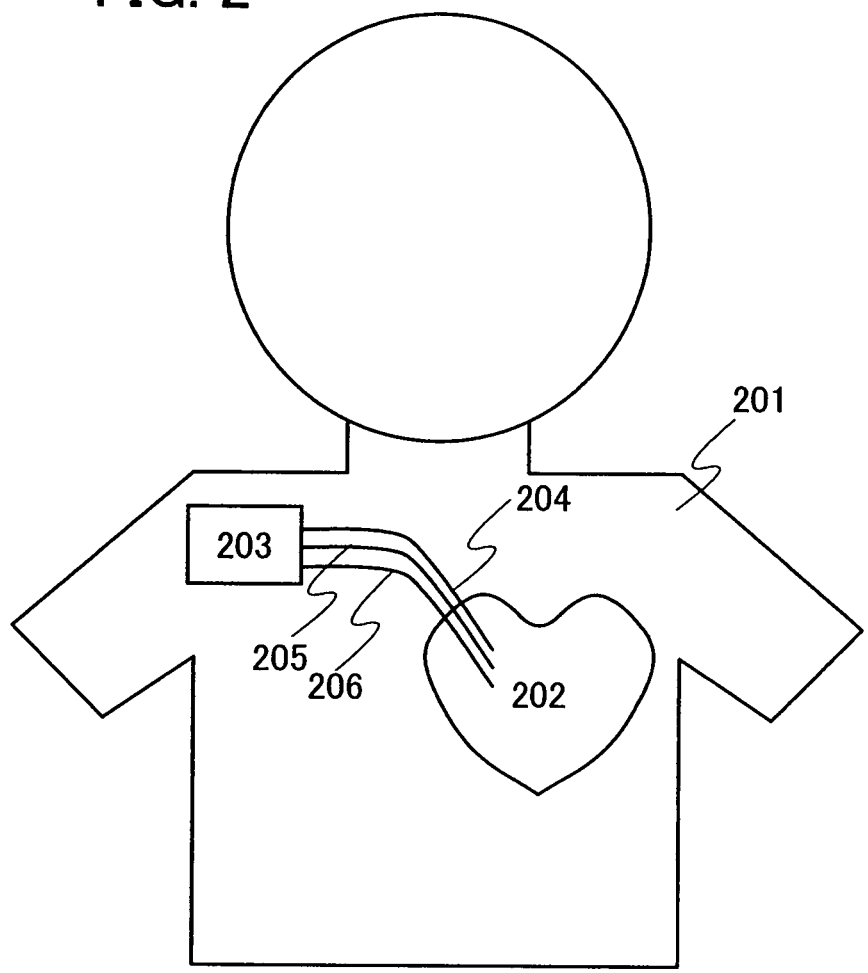
FIG. 2 is a conceptual view of a conventional cardiac pacemaker device.
Figure 3:
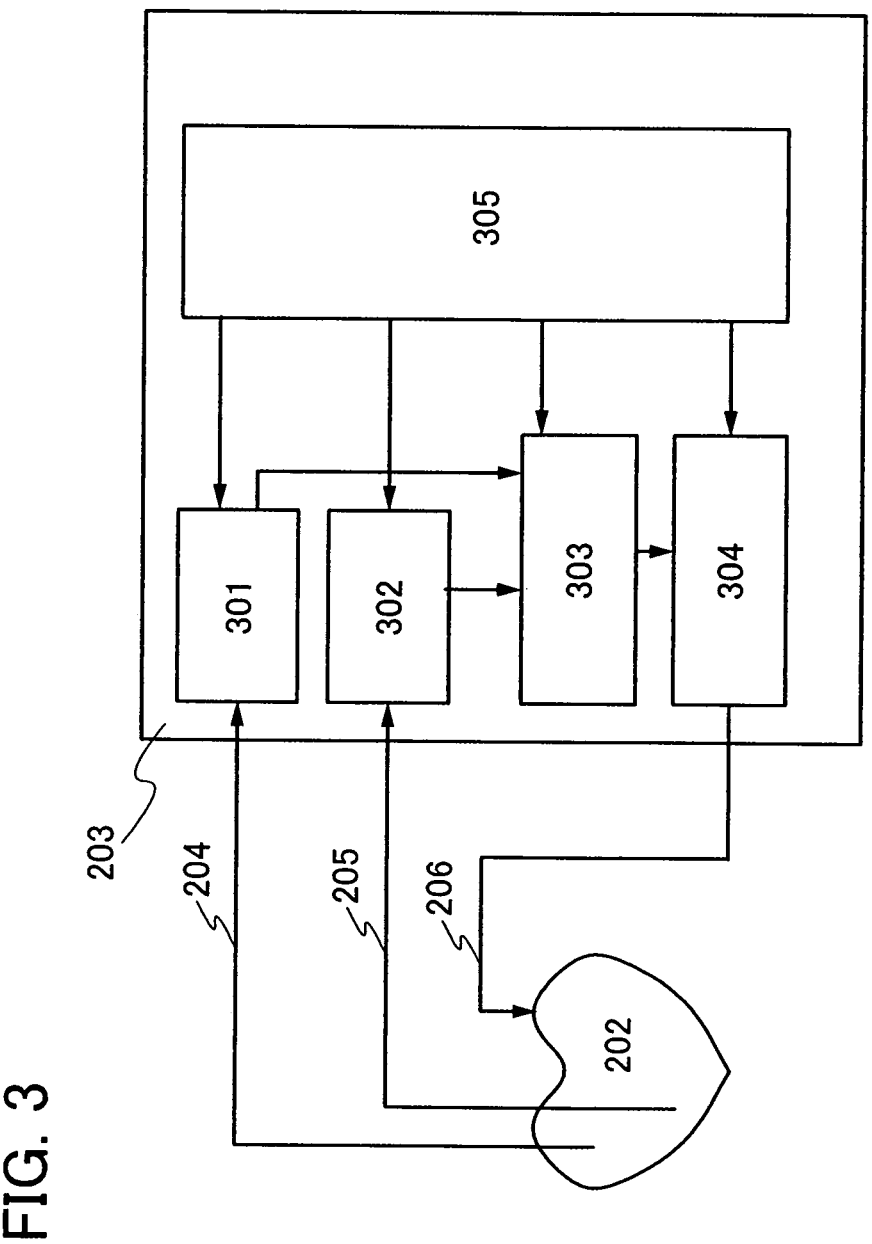
FIG. 3 is a block diagram of a conventional cardiac pacemaker device.

A cardiac pacemaker device of the present invention will be explained with reference to FIG. 1 and FIG. 5. FIG. 1 shows an embodiment mode of the cardiac pacemaker device according to this embodiment mode. This cardiac pacemaker device 102 includes an atrium detection amplifier circuit 103, a chamber detection amplifier circuit 104, a controller circuit 105, a pulse generation circuit 106, a secondary cell 107, an internal antenna 111, a rectifying and smoothing circuit 112, a charge circuit 113, and a charge control circuit 114. A secondary cell is employed as a battery in this embodiment mode; however, the battery is not limited thereto.

The atrium detection amplifier circuit 103 is connected to an atrium portion of a patient's heart 101 through a wiring 108. The chamber detection amplifier circuit 104 is connected to a chamber portion of the patient's heart 101 through a wiring 109. The atrium portion and the chamber portion each have one detection amplifier circuit in this embodiment mode; however, the number of detection amplifier circuits is not limited thereto. The number may also be one or more than two.

The atrium detection amplifier circuit 103 and the chamber detection amplifier circuit 104 detect and amplify electrocardiograms of the heart 101 and input the signals into the controller circuit 105. The controller 105 measures the amplified electrocardiograms and calculates a pulse cycle. Then, when the controller circuit 105 detects an irregular heartbeat, the signal is inputted into the pulse generation circuit 106. When the pulse generation circuit 106 receives the signal from the controller circuit 105, an electric signal is generated and an electroshock is delivered to the heart 101 through a wiring 110. The cardiac pacemaker device 102 operates in such a manner. As described above, the wiring for detecting pulses from the heart and the wiring for supplying an electric signal to the heart from the cardiac pacemaker device are provided independently; however, the present invention is not limited thereto and the wirings may also be provided in common.

The atrium detection amplifier circuit 103, the chamber detection amplifier circuit 104, the controller circuit 105, and the pulse generation circuit 106 are each supplied with power supply by the secondary cell 107. The secondary cell 107 is charged by an electric power which is transmitted wirelessly from an external antenna 115 and a transmitter 116.

Figure 5:
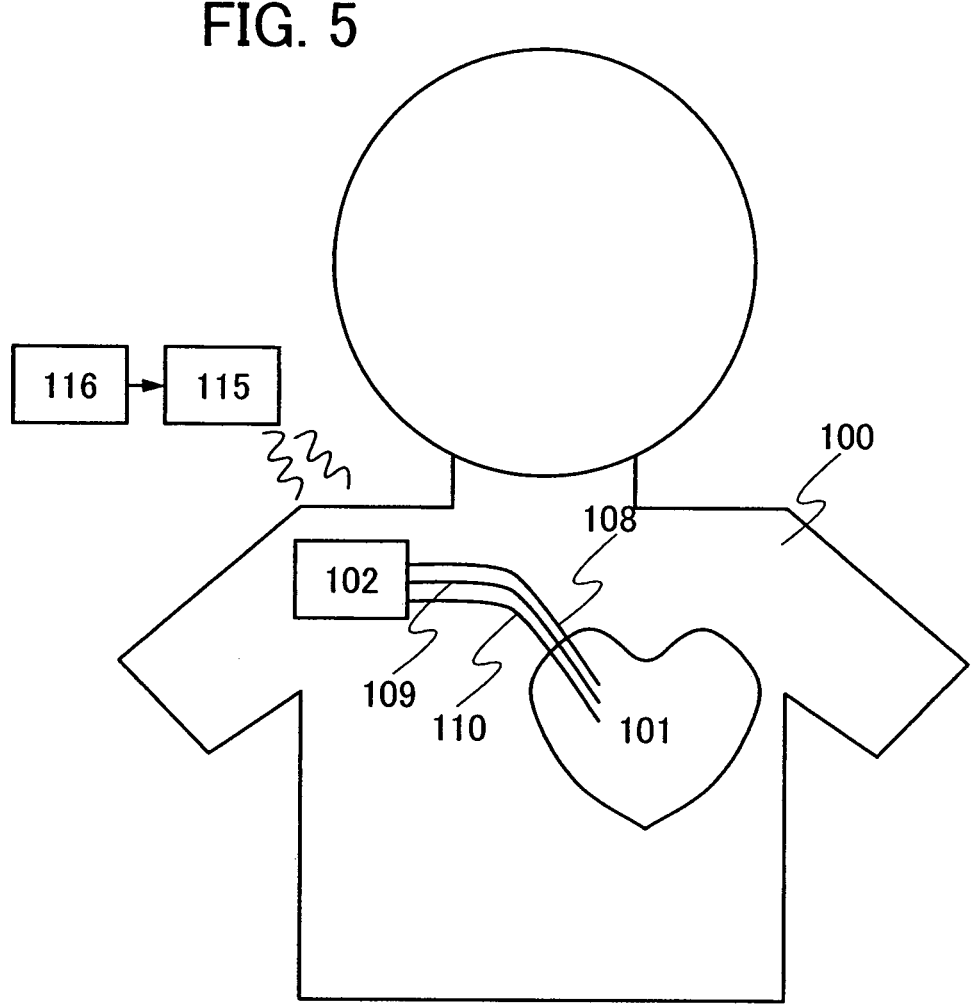
FIG. 5 is a conceptual view of a cardiac pacemaker device of the present invention.

FIG. 5 shows a schematic view of this embodiment mode. The heart 101 of a patient 100 and the cardiac pacemaker device 102 are connected through the wirings 108, 109, and 110. The transmitter 116 generates a wireless electromagnetic wave through the external antenna 115. The cardiac pacemaker device 102 receives the wireless electromagnetic wave, which is used as an operating power.

In FIG. 1, the internal antenna 111 receives a wireless signal generated by the external antenna 115. The signal received by the internal antenna 111 is inputted into the rectifying and smoothing circuit 112, and is converted into direct current. The charge circuit 113 generates current based on the electric power of the rectifying and smoothing circuit 112 to charge the secondary cell. The secondary cell 107 is monitored by the charge control circuit 114 so as not to be charged too much, and the charge circuit 113 is controlled and the charge amount is suppressed when the charge amount is excessively increased.

As described above, since the cardiac pacemaker device shown in this embodiment mode is wirelessly supplied with an electric power from outside the patient to store the battery and perform the circuit operation, there is no need to replace a cell. Therefore, there is no need for a patient to undergo a surgery for exchanging a cell, and suffering of a patient can be relieved.

Figure 4:
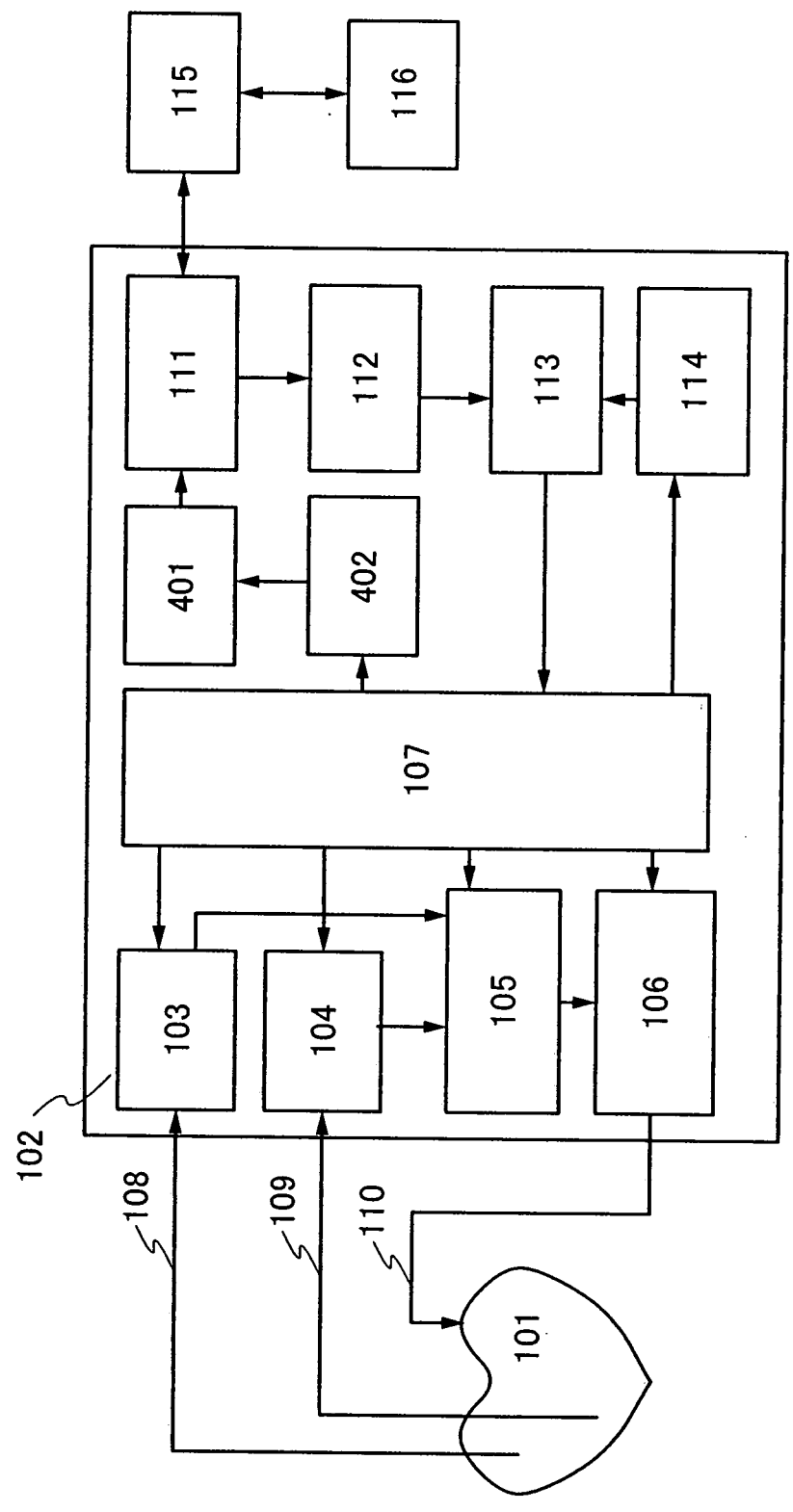
FIG. 4 is a block diagram of a cardiac pacemaker device of the present invention.

FIG. 4 shows an embodiment mode different from that of FIG. 1. In addition to the embodiment mode shown in FIG. 1, a residual amount detection circuit 402 and a modulation circuit 401 are added. An electric charge stored in a secondary cell 107 decreases gradually as a cardiac pacemaker device continues operating. Then, the voltage of the secondary 107 cell also decreases gradually. At the time when the voltage of the secondary cell 107 gets below minimum operating voltages of an atrium detection amplifier circuit 103, a chamber detection amplifier circuit 104, a controller circuit 105, and a pulse generation circuit 106, the cardiac pacemaker device cannot operate. In order to secure the security of a patient, it is necessary to add charge beforehand. Measures thereof will be mentioned in this embodiment mode.

Figure 14:
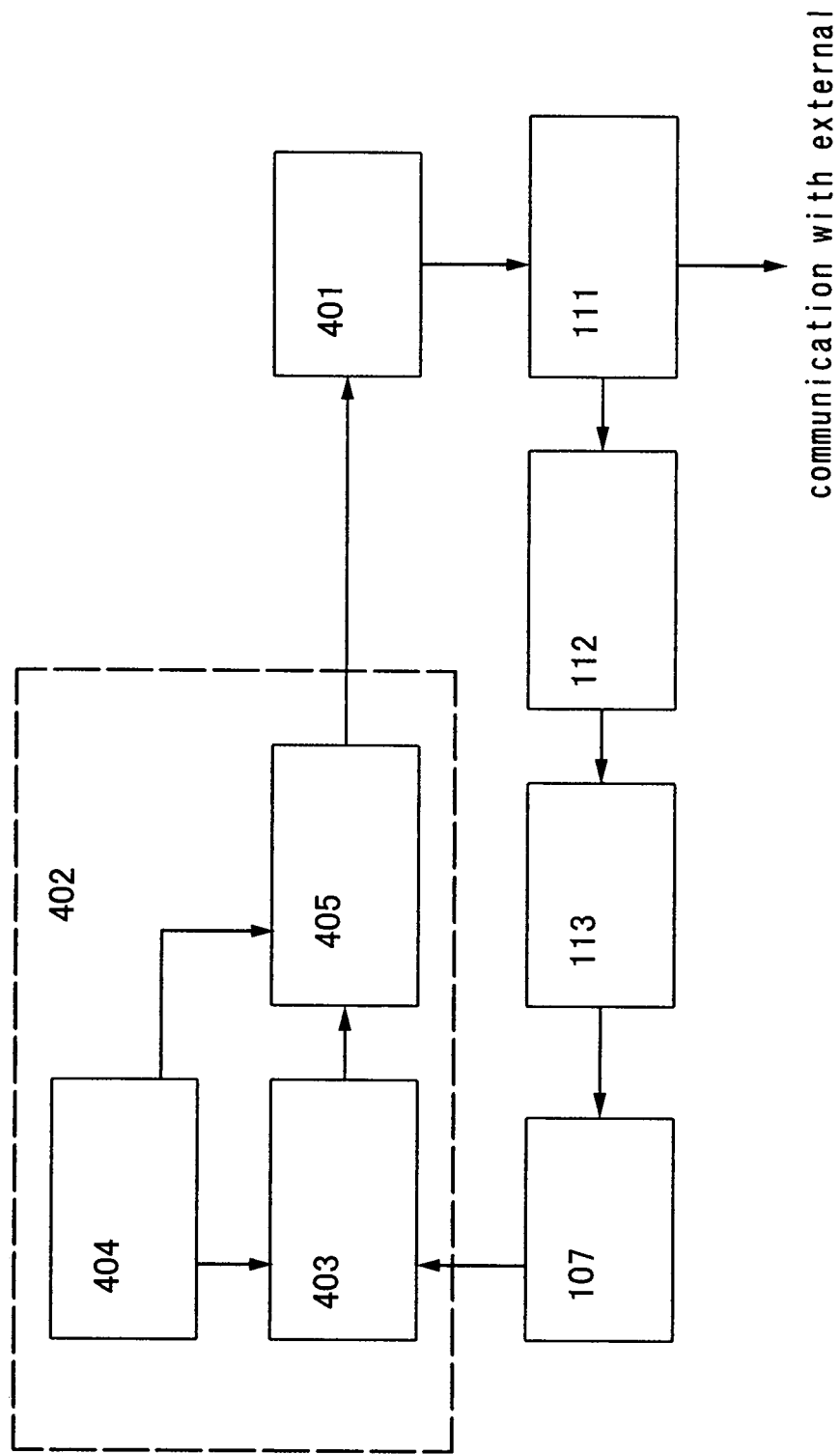
FIG. 14 is a block diagram of a residual amount detection circuit.

FIG. 14 shows a block diagram of the residual amount detection circuit 402. The residual amount detection circuit 402 shown in this embodiment mode includes an A/D conversion circuit 403, a clock generation circuit 404, and a logic circuit 405. Note that the residual amount detection circuit of the present invention is not limited to that shown in FIG. 14 and another residual amount detection circuit may also be used. The A/D conversion circuit 403 converts an output voltage of the secondary cell 107 into a digital output voltage.

The digitalized voltage data is inputted into the logic circuit 405. The logic circuit 405 encodes the digital voltage data. As an encode system, a deformation mirror code, a NRZ-L code, or the like can be used; however, the encode system is not limited thereto. The clock generation circuit 404 supplies the A/D conversion circuit 403 and the logic circuit 405 with clocks. The output of the logic circuit 405 is transmitted to the modulation circuit 401, and a wireless signal externally inputted is modulated.

In such a manner, the voltage of the secondary cell 107 can externally be monitored through the A/D conversion circuit 403, the logic circuit 405, the modulation circuit 401, and the internal antenna 111. When an electric charge stored in the secondary cell 107 decays and the voltage of the secondary cell 107 decreases, the modulated signal is monitored so that the necessity of charge can be confirmed.

Figure 15:
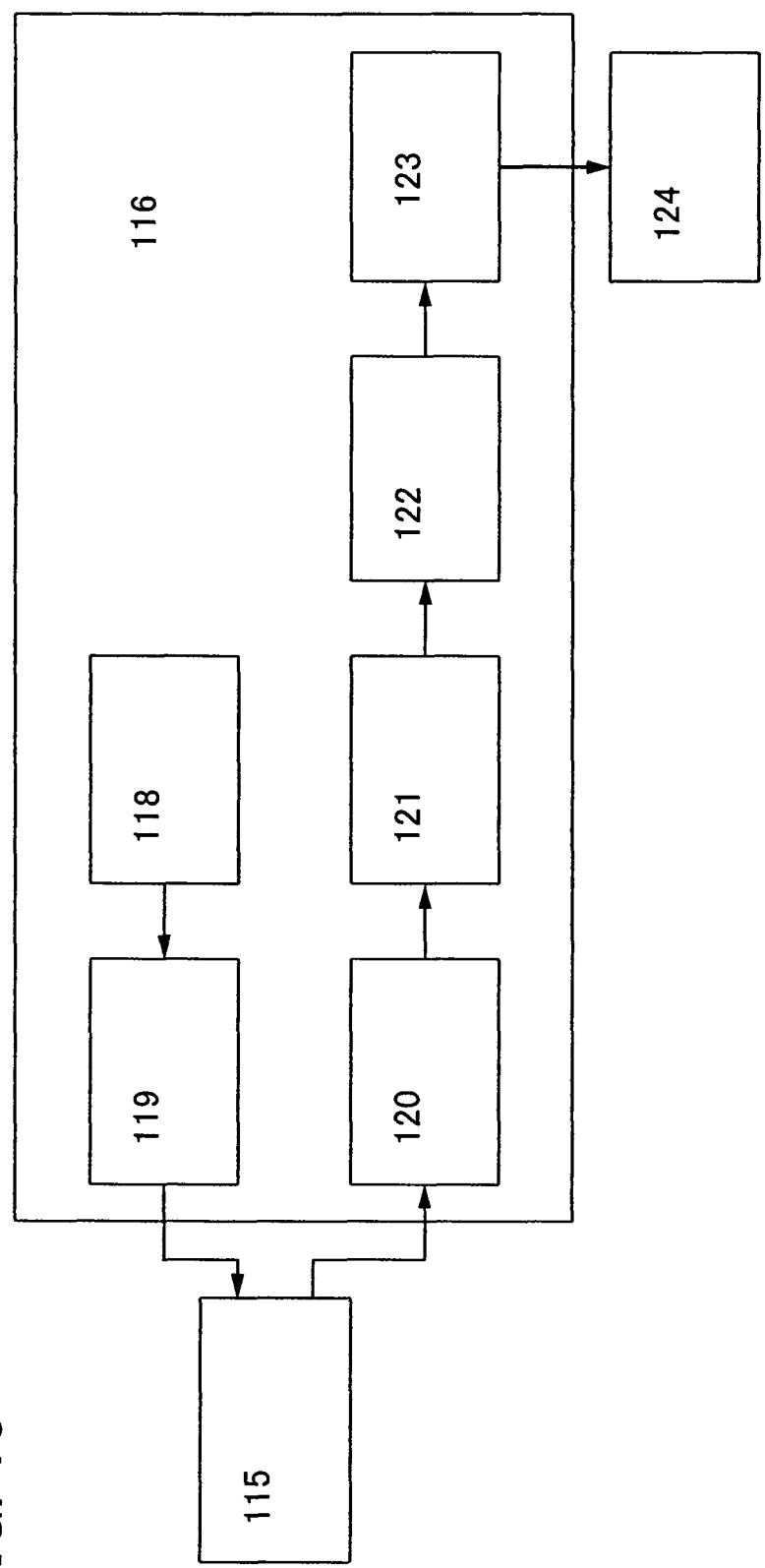
FIG. 15 is a block diagram of a transmitter.

FIG. 15 is an example of the transmitter 116 corresponding to the cardiac pacemaker device having the monitor function described above. The transmitter 116 includes an oscillation circuit 118, amplifier circuits 119 and 120, a demodulation circuit 121, a logic circuit 122, and a CPU 123. An output signal of the oscillation circuit 118 is amplified with the amplifier circuit 119, is transmitted to the cardiac pacemaker device from the external antenna 115, and then is used in order to charge a secondary cell. At this time, if the cardiac pacemaker device is in a monitor state, a signal of the external antenna 115 is modulated with the voltage data of the secondary cell. The amplifier circuit 120 amplifies the signal and demodulates the voltage data in the demodulation circuit 121.

Then, decode operation is performed in the logic circuit 122 so that a digital voltage data of the secondary cell, which is the source, can be taken out. This data is inputted into the CPU 123 to determine whether there is the necessity of charge. In addition, the result is displayed on a screen of a display device 124 so that the situation can be notified to the patient with eyes. If there is the necessity of charge, the charge is continued without change. If there is no necessity, the transmittance from the transmitter may also be stopped at the phase when the display confirmation is completed.

As described above, the cardiac pacemaker device of this embodiment mode can externally monitor the charge amount of the secondary cell and can make notification when the charge amount runs short. According to the present invention, there is no need for a patient to periodically undergo a surgery for exchanging a cell, and suffering of a patient can be relieved.

Embodiment 1

Figure 6:
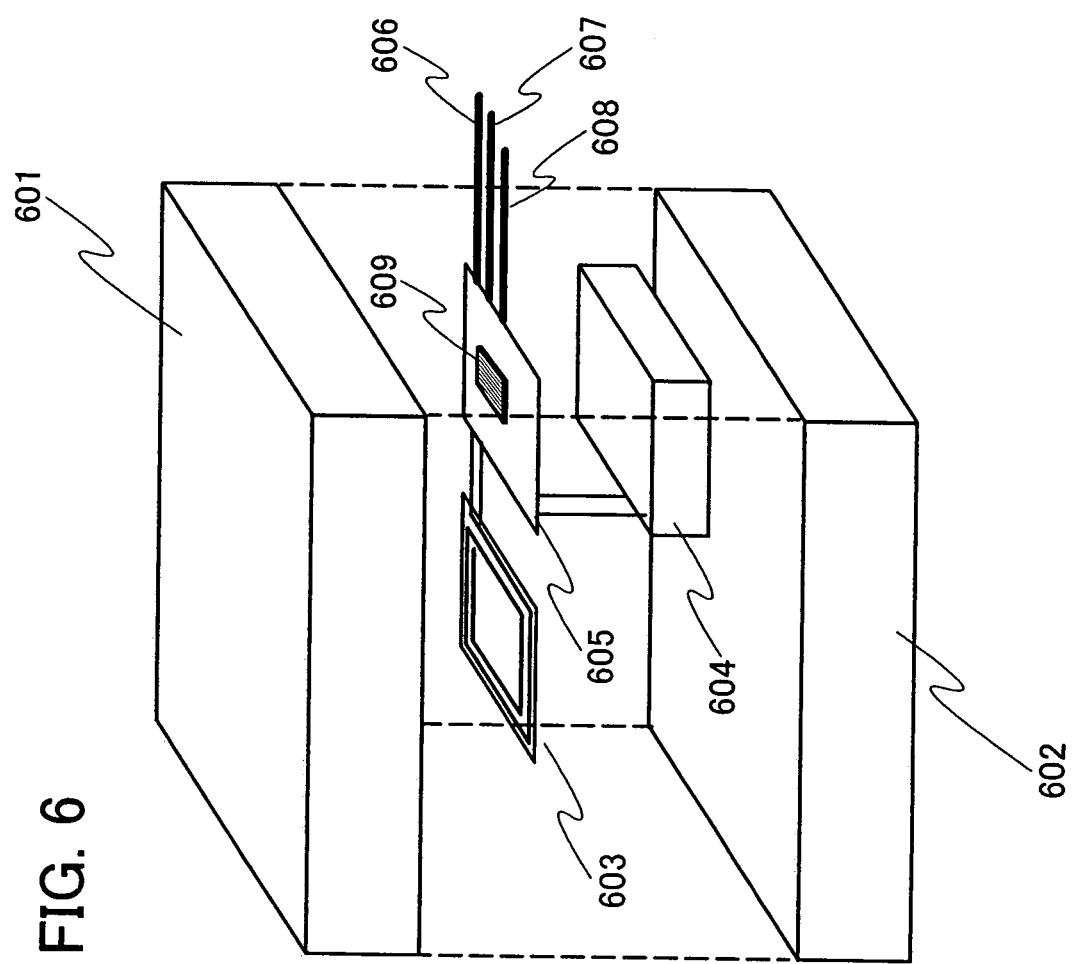
FIG. 6 is an external view of a cardiac pacemaker device of the present invention.

FIG. 6 shows a first embodiment. FIG. 6 shows a structure of a cardiac pacemaker device of the present invention. In this embodiment, the cardiac pacemaker device includes an upper-side chassis 601, a lower-side chassis 602, a built-in antenna 603, a secondary cell 604, a circuit board 605, wirings 606 and 607, and 608 reaching a heart.

Since the cardiac pacemaker device of this embodiment wirelessly obtains an electric power, an electromagnetic wave needs to reach inside the cardiac pacemaker device. The upper-side chassis 601 and the lower-side chassis 602 of the cardiac pacemaker device shown in this embodiment need to pass an electromagnetic wave; therefore, most of the upper-side chassis 601 and the lower-side chassis 602 are formed of an insulator. The upper-side chassis 601 and the lower-side chassis 602 are desirably formed of a resin. In addition, depending on the movement of a patient, the cardiac pacemaker device is subjected to various forces. The upper-side chassis 601 and the lower-side chassis 602 of the cardiac pacemaker device of this embodiment are desirably formed of a hard resin. Further, much desirably, it is advantageous to perform coating of the upper-side chassis 601 and the lower-side chassis 602 with DLC (diamond-like-carbon) in terms of reliability.

The built-in antenna 603 has a size for receiving a necessary electric power, and the size is desirably greater than or equal to 1 cm square. As for the secondary cell 604, one that can ensure long-term reliability is preferable and lithium ion secondary cell is desirable. However, the secondary cell 604 is not limited to the lithium ion secondary cell. An LSI 609 where an atrium detection amplifier circuit, a chamber detection amplifier circuit, a controller circuit, a pulse generation circuit, a rectifying and smoothing circuit, a charge circuit, and the like are integrated, accessories thereof, and the like are mounted on the circuit board 605. The circuit board 605 is made of a printed wiring board and formed of an epoxy resin or the like. It is desirable that the LSI 609 reduce the package size to diminish the installation area using a chip-size packaging technology or a multi-chip packaging technology. A chip-penetration technique for polishing and stacking a chip to pass through the contact may be used. The wirings 606, 607, 608 reaching a heart are connected to the heart from the circuit board 605 and touch a patient's organ out of the chassis. Therefore, sealing is performed so that a patient's biological fluid does not penetrate inside the cardiac pacemaker device from the wirings.

In addition, the circuit board 605 may also be subjected to shielding treatment so that the detection amplifier circuit or the controller circuit does not malfunction by the electromagnetic wave which is supplied from outside a patient's body in order to supply an electric power.

As described above, the secondary cell can wirelessly be charged from outside the cardiac pacemaker device of this embodiment, and it becomes possible to relieve a patient from physical suffering for exchanging a cell.

Embodiment 2

Figure 7:
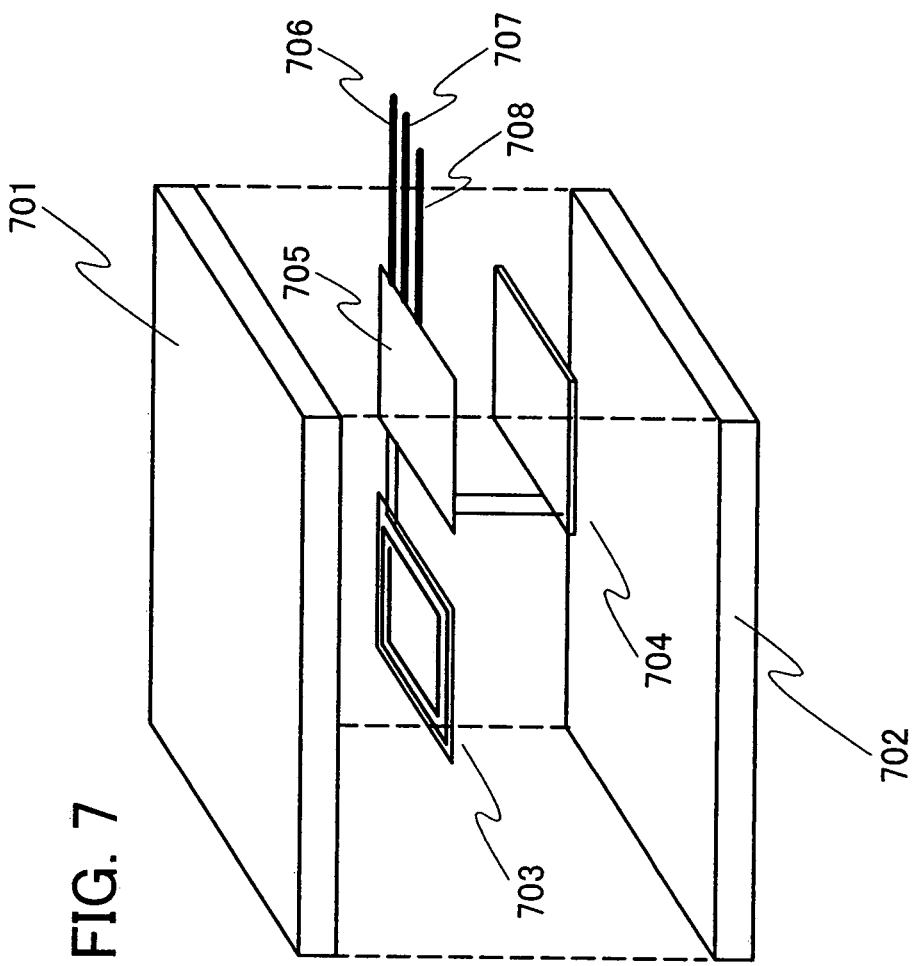
FIG. 7 is an external view of a cardiac pacemaker device of the present invention.

FIG. 7 shows a second embodiment. A cardiac pacemaker device of this embodiment in FIG. 7 includes an upper-side chassis 701, a lower-side chassis 702, a built-in antenna 703, a thin film secondary cell 704, a circuit board 705, and wirings 706, 707, and 708 reaching a heart. The thin film secondary cell is formed of a lithium compound, and the thickness thereof can be made less than or equal to 10 μm. In addition, the circuit board 705 can be formed with a flexible thin film circuit film with the use of a thin film transistor. In such a case, the thickness of the circuit board 705 can be made less than or equal to 100 μm. Moreover, by the built-in antenna formed over a flexible substrate, the thickness can also be made less than or equal to 100 μm. As described above, the thickness of the upper-side chassis 701 and the lower-side chassis 702 can be made less than or equal to 0.5 mm. Therefore, the thickness of the cardiac pacemaker device of this embodiment can be made less than or equal to 1 mm. This brings less discomfort even when the cardiac pacemaker device is implanted into a patient's body; thus, the patient can be relieved from the burden.

Since the cardiac pacemaker device of this embodiment wirelessly obtains an electric power, an electromagnetic wave needs to reach inside the cardiac pacemaker device. The upper-side chassis 701 and the lower-side chassis 702 of the cardiac pacemaker device shown in this embodiment need to pass an electromagnetic wave; therefore, most of the upper-side chassis 701 and the lower-side chassis 702 are formed of an insulator. The upper-side chassis 701 and the lower-side chassis 702 are desirably formed of a resin. In addition, depending on the movement of a patient, the cardiac pacemaker device is subjected to various forces. The upper-side chassis 701 and the lower-side chassis 702 of the cardiac pacemaker device of this embodiment are desirably formed of a hard resin. Further, much desirably, it is advantageous to perform coating of the upper-side chassis 701 and the lower-side chassis 702 with DLC (diamond-like-carbon) in terms of reliability.

The wirings 706, 707, 708 reaching a heart are connected to the heart from the circuit board 705 and touch a patient's organ out of the chassis. Therefore, sealing is performed so that a patient's biological fluid does not penetrate inside the cardiac pacemaker device from the wirings.

In addition, the circuit board 705 may also be subjected to shielding treatment so that a detection amplifier circuit or a controller circuit does not malfunction by the electromagnetic wave which is supplied from outside a patient's body in order to supply an electric power.

In the embodiment shown in FIG. 7, all circuits mounted on the circuit board are formed of thin film transistors; however, the circuits are not limited thereto. A structure may also be employed where a rectifying and smoothing circuit, a charge circuit, a charge control circuit, and the like are formed of thin film transistors, while an atrium detection amplifier circuit, a chamber detection amplifier circuit, a controller circuit, a pulse generation circuit, and the like are formed of LSI using single-crystal transistors. The combination of a thin film transistor and a single-crystal transistor can be set arbitrarily.

As described above, the thin film secondary cell can wirelessly be charged from outside the cardiac pacemaker device of this embodiment, and it becomes possible to relieve a patient from physical suffering for exchanging a cell.

Embodiment 3

Hereinafter, the thin film secondary cell used in Embodiment 2 will be explained. There is a nickel-cadmium cell, a lithium-ion secondary cell, a lead cell, or the like as a secondary cell, and a lithium-ion cell is widely used due to the advantage such as lack of a memory effect and the large current amount.

In addition, research on thinning a lithium-ion cell has recently been carried out and a lithium-ion cell having a thickness of 1 to several μm has been manufactured. Such a thin film secondary cell can be utilized as a flexible secondary cell.

Figure 8:
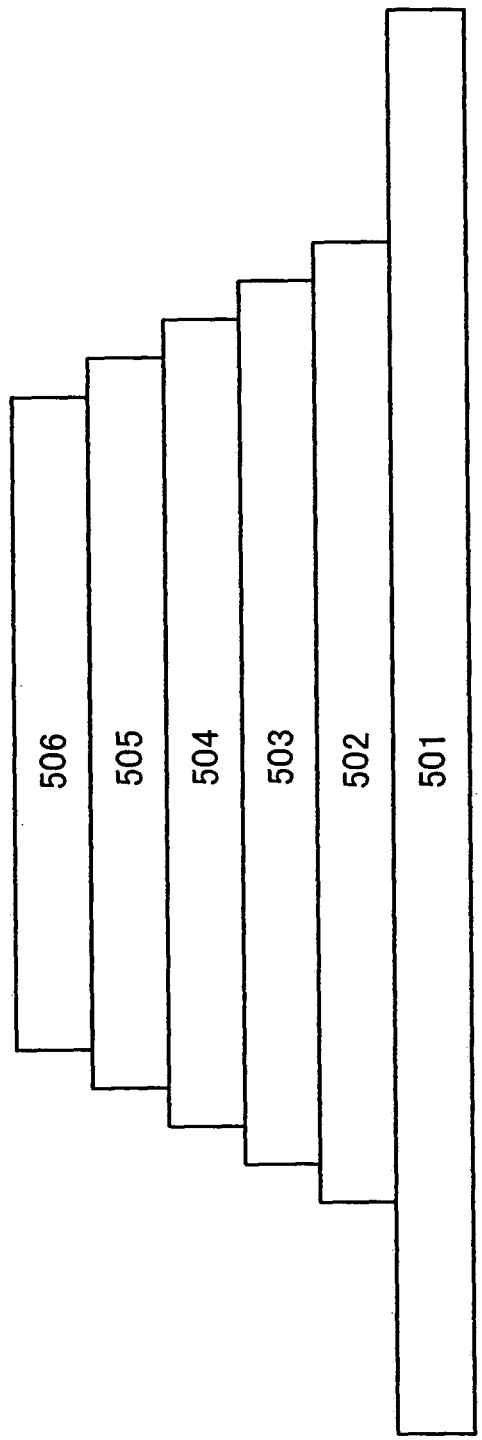
FIG. 8 is a cross-sectional view of a thin film secondary cell.

FIG. 8 shows an example of the thin film secondary cell, which is a cross-sectional example of a lithium-ion thin film cell. A collector thin film 502 to be an electrode is formed over a substrate 501. The collector thin film 502 has favorable adhesiveness to an anode active material layer 503 and needs to have low resistance; thus, aluminum, copper, nickel, vanadium, or the like can be used. The anode active material layer 503 is formed over the collector thin film 502. Vanadium oxide or the like is generally used for the anode active material layer 503. A solid electrolyte layer 504 is formed over the anode active material layer 503. Lithium phosphorus oxide or the like is generally used for the solid electrolyte layer 504. A cathode active material layer 505 is formed over the solid electrolyte layer 504. Lithium manganese oxide or the like is generally used for the cathode active material layer 505. Lithium cobalt oxide or lithium nickel oxide may also be used. A collector thin film 506 to be an electrode is formed over the cathode active material layer 505. The collector thin film 506 needs to have favorable adhesiveness to the cathode active material layer 505 and low resistance; thus, aluminum, copper, nickel, vanadium, or the like can be used. Each of these thin film layers may also be formed using a sputtering technique or an evaporation technique. Each thickness is desirably 0.1 to 3 μm.

Next, hereinafter, operations at the time of charging and discharging will be explained. At the time of charging, lithium is separated from the cathode active material layer 505 to be an ion. The lithium ion is absorbed by the anode active material layer 503 through the solid electrolyte layer 504. At this time, electrons are discharged outside from the cathode active material layer 505. At the time of discharging, lithium is separated from the anode active material layer 503 to be an ion. The lithium ion is absorbed by the cathode active material layer 505 through the solid electrolyte layer 504. At this time, electrons are discharged outside from the anode active material layer 503. In such a manner, the thin film secondary cell operates.

With the use of the thin film secondary cell described in this embodiment, a thinner cardiac pacemaker device can be manufactured; thus, a cardiac patient can be relieved from the suffering.

Embodiment 4

Figure 9:
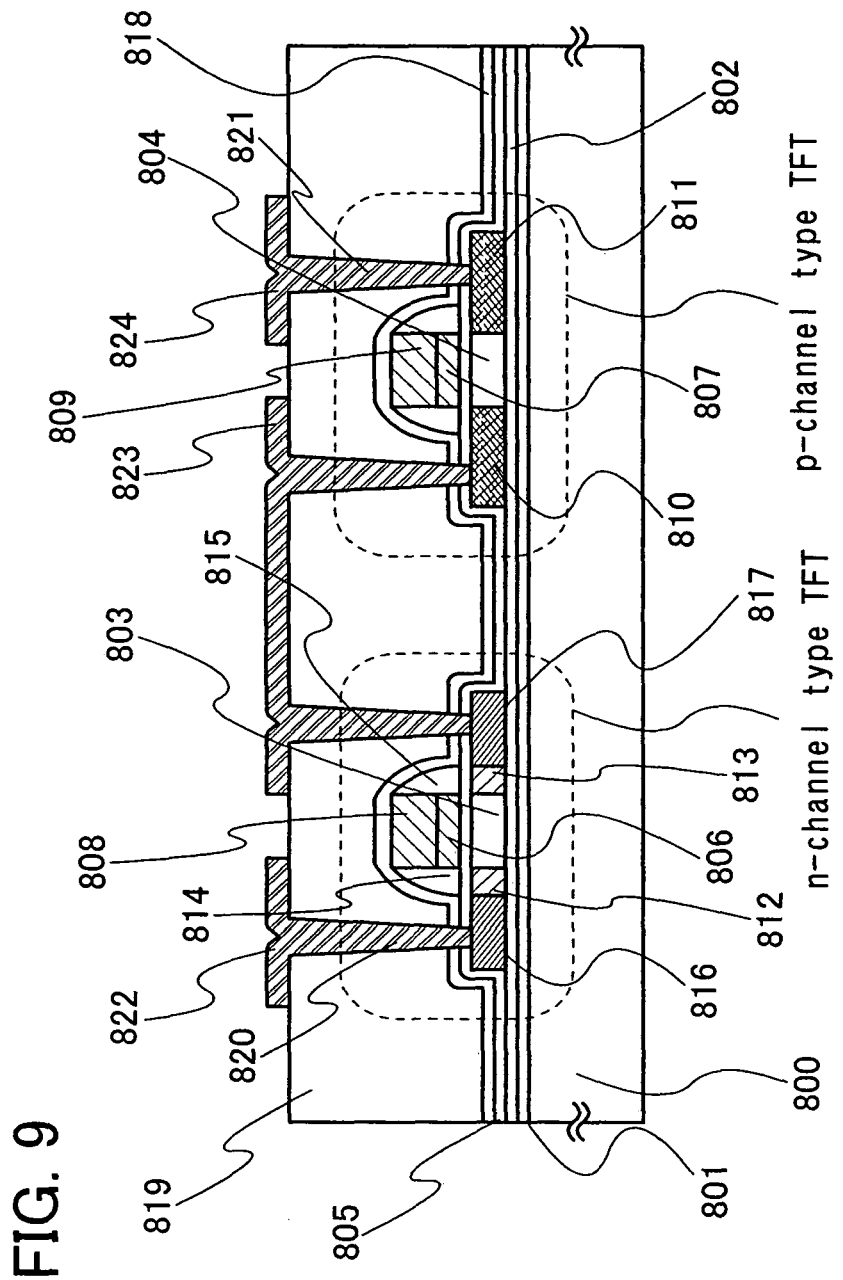
FIG. 9 is a cross-sectional view of a TFT.

As Embodiment 4, a method for manufacturing the thin film transistor described in Embodiment 2 will be explained with reference to FIG. 9. Note that, in this embodiment, an n-channel thin film transistor (hereinafter, referred to as a TFT) and a p-channel type TFT are taken as examples of semiconductor elements; however, the semiconductor elements are not limited thereto in the present invention. In addition, this manufacturing method is just an example and does not limit a manufacturing method of a semiconductor element.

First, over an insulating substrate 800, base films 801 and 802 formed of an insulating film such as a silicon oxide film, a silicon nitride film, a silicon oxynitride film, or the like are formed. For example, a silicon oxynitride film is formed with a thickness of 10 to 200 nm as the base film 801, and a hydrogenated silicon oxynitride film is formed with a thickness of 50 to 200 nm as the base film 802 to be sequentially stacked.

Island-shaped semiconductor layers 803 and 804 are formed of a crystalline semiconductor film which is manufactured with a semiconductor film having an amorphous structure using a known laser crystallization method or thermal crystallization method. These island-shaped semiconductor layers 803 and 804 are formed with a thickness of 25 to 80 nm. The material of the crystalline semiconductor film is not limited; however, silicon, a silicon-germanium (SiGe) alloy, or the like is preferably used.

Next, a gate insulating film 805 is formed so as to cover the island-shaped semiconductor layers 803 and 804. The gate insulating film 805 is formed of an insulating film containing silicon by a plasma CVD method or a sputtering method so as to have a thickness of greater than or equal to 10 nm and less than or equal to 80 nm.

Then, first conductive layers 806 and 807 are formed over the gate insulating film 805. Subsequently, second conductive layers 808 and 809 are formed, and the stack of the first conductive layer 806 and the second conductive layer 808 and the stack of the first conductive layer 807 and the second conductive layer 809 are etched at a time, whereby gate electrodes of TFTs are formed.

In this embodiment, the first conductive layers 806 and 807 are formed of TaN with a thickness of 50 to 100 nm, while the second conductive layers 808 and 809 are formed of W with a thickness of 100 to 300 nm. However, the material of the conductive layers is not particularly limited, and each may be formed of an element of Ta, W, Ti, Mo, Al, Cu, and the like, or an alloy or a compound containing the element as its main component.

Next, a p-channel type TFT is doped with an element imparting p-type conductivity to form first impurity regions 810 and 811. Subsequently, an n-channel type TFT is doped with an element imparting n-type conductivity to form second impurity regions 812 and 813 in order to form an LDD region thereof. Thereafter, sidewalls 814 and 815 are formed and the n-channel type TFT is doped with an element imparting n-type conductivity to form third impurity regions 816 and 817. Such doping methods may be performed by an ion doping method or an ion implantation method. Through these steps, the impurity regions are each formed in the island-shaped semiconductor layers.

Then, the impurity elements each added to the island-shaped semiconductor layers are activated. This step is performed by a thermal annealing method using an annealing furnace. Moreover, a laser annealing method or a rapid thermal annealing (RTA) method may be adopted. Further, the island-shaped semiconductor layers are hydrogenated by application of heat treatment at a temperature of 300 to 450° C. for 1 to 12 hours in an atmosphere containing 3 to 100% of hydrogen. Plasma hydrogenation (using hydrogen excited by plasma) may also be performed as another means of hydrogenation.

A first interlayer insulating film 818 is formed of a silicon oxynitride film. The thickness of the first interlayer insulating film 818 is made 10 to 80 nm similarly to the thickness of the gate insulating film. Subsequently, a second interlayer insulating film 819 is formed of an organic insulating material such as acrylic. Instead of the organic insulating material, an inorganic material may also be used for the second interlayer insulating film 819. As the inorganic material, inorganic $SiO_2$, $SiO_2$ obtained by a plasma CVD method (PCVD-$SiO_2$), a silicon oxide film applied by a SOG (Spin On Glass) method, or the like is used.

Next, contact holes 820 and 821 are formed. In addition, electrodes 822 to 824 in contact with source and drain regions of the island-shaped semiconductor layers are formed.

As described above, the n-channel type TFT with an LDD structure and the p-channel type TFT with a single drain structure can be formed over the substrate.

In this embodiment, a manufacturing method up to the step of forming a circuit portion and transferring the circuit portion to a flexible substrate will be explained with reference to FIGS. 10A and 10B and FIGS. 11A and 11B. Note that, in this embodiment, an n-channel type TFT and a p-channel type TFT are taken as examples of semiconductor elements; however, the semiconductor elements of the present invention is not limited thereto in the present invention. In addition, this manufacturing method is just an example and does not limit a manufacturing method of a semiconductor element over an insulating substrate.

First, a peeling layer 900 is formed over the insulating substrate 800. The peeling layer 900 can be formed by a sputtering method, a plasma CVD method, or the like using a layer containing silicon as its main component, such as amorphous silicon, polycrystalline silicon, single crystalline silicon, or microcrystalline silicon (including semi-amorphous silicon). In this embodiment, amorphous silicon having a thickness of approximately 500 nm is formed by a sputtering method to be used as the peeling layer 900. Subsequently, such a circuit portion as shown in FIG. 9 is formed in accordance with an operation process described above.

Next, a third interlayer insulating film 901 is formed over the second interlayer insulating film 819 to form pads 902 and 903. The pads 902 and 903 are formed using a conductive material including one or more of metals such as Ag, Au, Cu, Pd, Cr, Mo, Ti, Ta, W, and Al, or metal compounds thereof.

A protective layer 904 is formed over the third interlayer insulating film 901 so as to cover the pads 902 and 903. The protective layer 904 is formed of a material that can protect the pads 902 and 903 when the peeling layer 900 will subsequently be etched away. For example, the protective layer 904 can be formed by application of, over the entire surface, an epoxy-based resin, an acrylate-based resin, or a silicone-based resin that is soluble in water or alcohols (FIG. 10A).

Then, a groove 905 for isolating the peeling layer 900 is formed to such a degree that the peeling layer 900 is exposed (see FIG. 10B). The groove 905 can be formed by a method of etching, dicing, scribing, or the like.

Figure 11A:
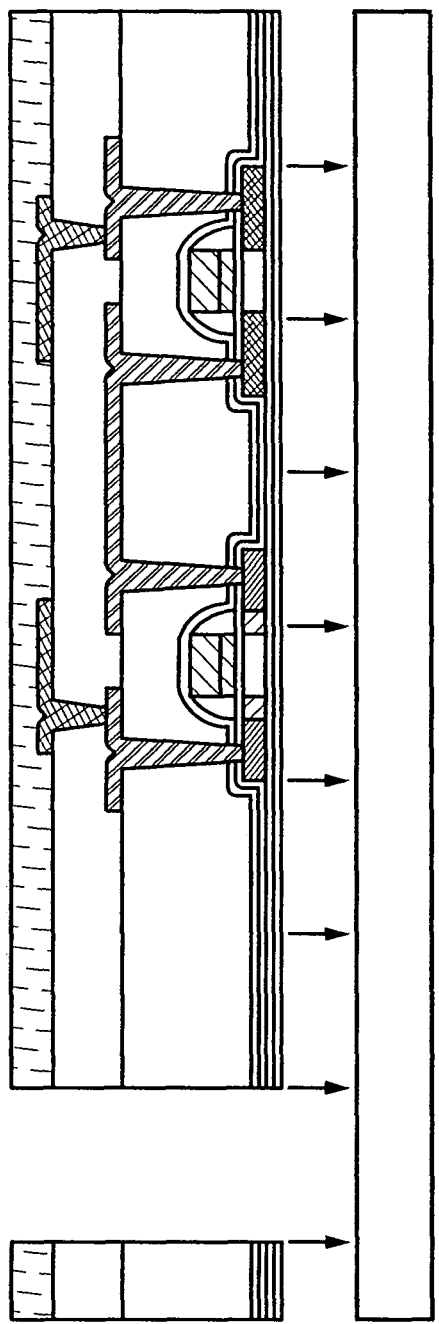
FIGS. 11A and 11B are each a cross-sectional view of a TFT.

Subsequently, the peeling layer 900 is etched away (see FIG. 11A). In this embodiment, halogen fluoride is used as an etching gas and introduced through the groove 905. In this embodiment, etching is performed for three hours using, for example, $ClF_3$ (chlorine trifluoride) at a temperature of 350° C., a flow rate of 300 sccm, and a pressure of 798 Pa. Alternatively, a $ClF_3$ gas mixed with nitrogen may also be used. The peeling layer 900 is selectively etched using halogen fluoride such as $ClF_3$; thus, the insulating substrate 800 can be peeled off. Note that halogen fluoride may be either a gas or a liquid.

Figure 11B:
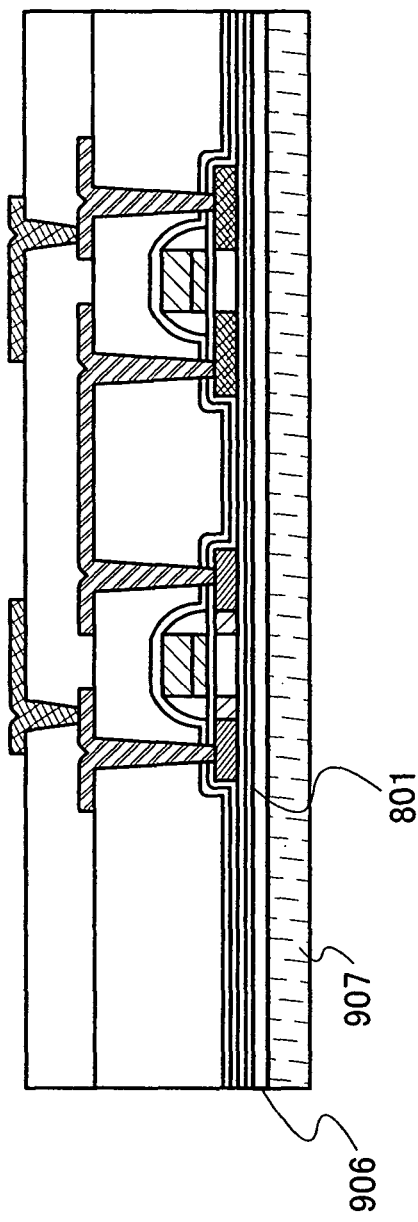

Next, the peeled circuit portion is attached to a support base 907 with an adhesive 906 (see FIG. 11B). The adhesive 906 is formed of a material capable of attaching the support base 907 to the base film 801. As the adhesive 906, for example, various curable adhesives can be used such as a reactive curable adhesive, a thermosetting adhesive, a photo-curable adhesive such as an ultraviolet curable adhesive, and an anaerobic adhesive.

For the support base 907, an organic material such as flexible paper or flexible plastic can be used. Alternatively, the support base 907 may be formed of a flexible inorganic material. It is desirable that the support base 907 have high thermal conductivity of approximately 2 to 30 W/mK in order to disperse the heat generated in an integrated circuit.

A method of peeling off the circuit portion from the insulating substrate 800 is not limited to the method using the etching of the silicon film as shown in this embodiment, and various other methods can also be used. For example, there are a method where a metal oxide film is formed between a substrate with high heat resistance and an integrated circuit, and the metal oxide film is weakened by crystallization to be able to peel off the integrated circuit; a method where a peeling layer is broken by laser irradiation to be able to peel off an integrated circuit from a substrate; and a method where a substrate on which an integrated circuit is formed is removed mechanically or by etching using a solution or a gas to be able to peel off the integrated circuit from the substrate.

Embodiment 5

Figure 12:
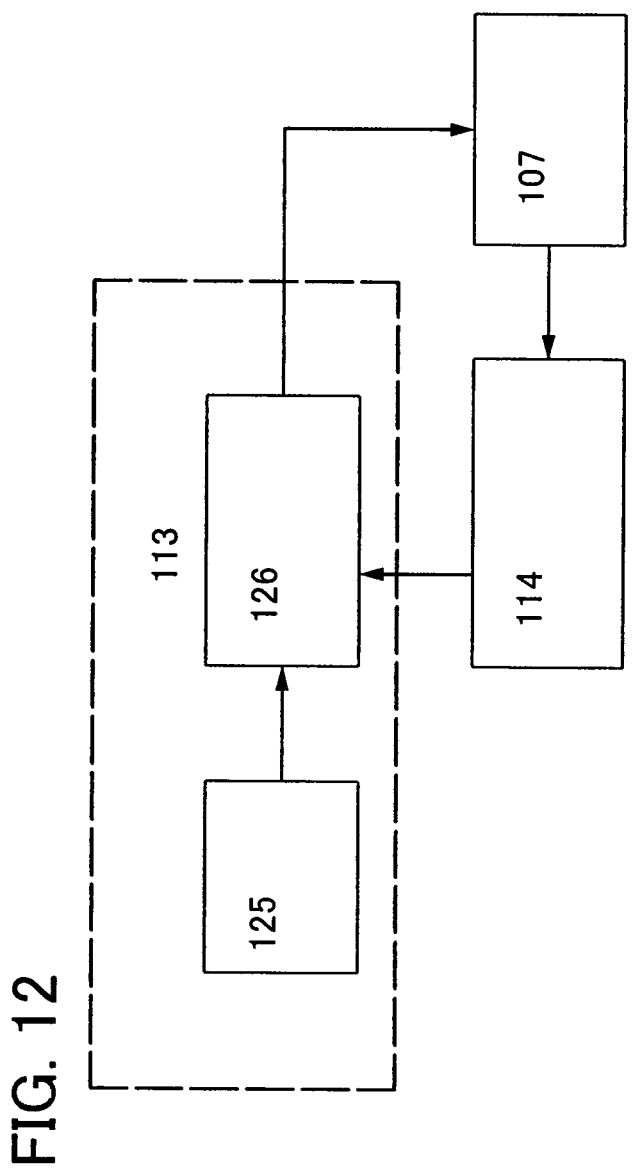
FIG. 12 is a block diagram of a charge circuit.

When a secondary cell is used as a battery, generally, it is necessary to control the charge and discharge. It is necessary to charge the secondary cell while a charge situation is monitored so that the secondary cell is not overcharged at the time of the charge. When the charge of the secondary cell used in the present invention is controlled, a special circuit is needed. FIG. 12 shows a block diagram for controlling the charge.

In an example shown in FIG. 12, a charge circuit 113 includes a constant current source 125 and a switching circuit 126. The charge circuit 113 is connected to a charge control circuit 114 and a secondary cell 107. The charge control circuit 114 described here, which is just an example, is not limited to such a structure and other structures may also be employed. In this embodiment, the secondary cell is charged by the constant current; however, instead of charge only by the constant current, the charge by the constant current may also be switched to a charge by a constant voltage at a certain point. Alternatively, another method without a constant current may also be employed. Moreover, transistors that form the following circuits may be a thin film transistor, a transistor using a single-crystal substrate, or an organic transistor.

Figure 13:
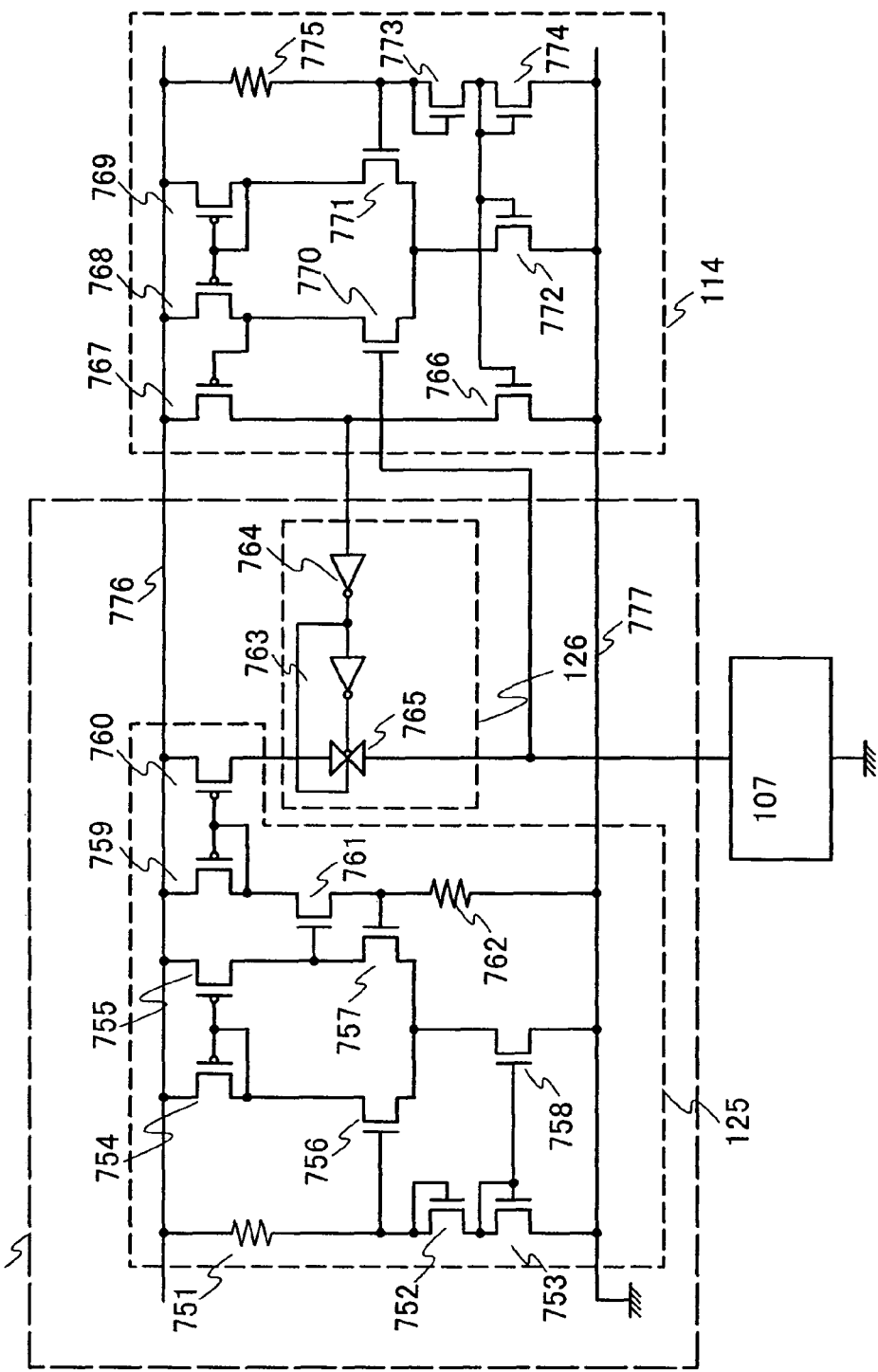
FIG. 13 is a circuit diagram of a charge circuit.

FIG. 13 shows the circuit of FIG. 12 in more detail. Hereinafter, operations thereof will be explained. The constant current source 125, the switching circuit 126, and the charge control circuit 114 each use a high-potential power supply line 776 and a low-potential power supply line 777 as power supply lines. The low-potential power supply line 777 is used as a GND line in FIG. 13; however, without limitation to a GND line, the low-potential power supply line 777 may also be used as other potential.

The constant current source 125 includes transistors 752 to 761 and resistors 751 and 762. Current flows through the transistors 752 and 753 from the high-potential power supply line 776 through the resistor 751; thus, the transistors 752 and 753 are turned on.

The transistors 754, 755, 756, 757, and 758 form a feedback differential amplifier circuit, and the gate potential of the transistor 757 is almost the same as the gate potential of the transistor 752. The value of the drain current of the transistor 761 is obtained by division of a difference between the gate potential of the transistor 757 and the potential of the low-potential power supply line 777 by the resistance of the resistor 762. The current is inputted into a current mirror circuit formed of the transistors 759 and 760, and the output current of the current mirror circuit is supplied to the switching circuit 126. The constant current source 125 is not limited to this structure and other structures may also be employed.

The switching circuit 126 includes a transmission gate 765 and inverters 763 and 764. Whether the current of the constant current source 125 is supplied to the secondary cell 107 or not is controlled by an input signal of the inverter 764. The switching circuit is not limited to this structure and other structures may also be employed.

The charge control circuit 114 includes transistors 766 to 774 and a resistor 775. Current flows through the transistors 773 and 774 from the high-potential power supply line 776 through the resistor 775; thus, the transistors 773 and 774 are turned on. The transistors 768, 769, 770, 771, and 772 form a differential comparator. When the gate potential of the transistor 770 is lower than the gate potential of the transistor 771, the drain potential of the transistor 768 is almost equivalent to the potential of the high-potential power supply line 776. When the gate potential of the transistor 770 is higher than the gate potential of the transistor 771, the drain potential of the transistor 768 is almost equivalent to the source potential of the transistor 770.

When the drain potential of the transistor 768 is almost equivalent to the high-potential power supply line, the charge control circuit outputs low through a buffer including the transistors 767 and 766. When the drain potential of the transistor 768 is almost equivalent to the source potential of the transistor 770, the charge control circuit outputs high through the buffer including the transistors 767 and 766.

When the output of the charge control circuit 114 is low, a current is supplied to the secondary cell 107 through the switching circuit 126. In addition, when the output of the charge control circuit 114 is high, the switching circuit 126 is turned off and no current is supplied to the secondary cell 107. Since the gate of the transistor 770 is connected to the secondary cell 107, the secondary cell 107 is charged, and the charge is stopped when the potential exceeds a threshold value of the comparator of the charge control circuit 114. The threshold value of the comparator is set depending on the gate potential of the transistor 773 in this embodiment; however, the threshold value is not limited thereto and other potential may also be employed. In general, predetermined potential is appropriately determined depending on the use of the charge control circuit 114 and the performance of the secondary cell.

The charge circuit for the secondary cell is formed with the structure described above in this embodiment; however, the structure is not limited thereto.

Embodiment 6

FIG. 16 shows an embodiment where a transmitter 116 and an external antenna 115 are incorporated into wearing clothes 127. The external antenna 115 and the transmitter 116 are incorporated so as to overlap almost with the position of a cardiac pacemaker device 102 implanted into a patient 100; therefore, a battery incorporated into the cardiac pacemaker device 102 can be charged efficiently. In addition, since the patient's both hands are free, the patient can be engaged in other work at the time of the charge. The convenience of the patient can be improved in accordance with this embodiment.

This embodiment shows an example where the transmitter and the external antenna are incorporated into wearing clothes; however, besides, a transmitter, an external antenna, or the like may be incorporated into a belt or the like. Moreover, the position of the external antenna and the transmitter does not need to be the same, and the external antenna may be placed near the cardiac pacemaker device and the transmitter may be placed at a waist or a head. In accordance with this embodiment, the battery of the cardiac pacemaker device can be charged efficiently.

The present application is based on Japanese Patent Application serial No. 2006-155300 filed on Jun. 2, 2006 in Japan Patent Office, the entire contents of which are hereby incorporated by reference.

What is claimed is:

1. A device comprising:
a battery;
a first circuit for supplying an electric signal to a heart;
a second circuit for monitoring a voltage of the battery and converting the voltage into a digital signal;
an antenna for receiving a wireless signal transmitted from an external device;
a rectifying and smoothing circuit converting the wireless signal received by the antenna into direct current;
a charge circuit for generating current based on an electric power of the rectifying and smoothing circuit and charging the battery, the charge circuit comprising a constant current source and a switch circuit;
a charge control circuit for monitoring the voltage of the battery; and
a modulation circuit for modulating the digital signal, the modulation circuit connected to the second circuit and the antenna,
wherein the modulated wireless signal is transmitted to the external device through the antenna,
wherein the battery is connected to the first circuit, the second circuit, the charge circuit, and the charge control circuit,
wherein a first terminal of the switch circuit is electrically connected to the constant current source,
wherein a second terminal of the switch circuit is electrically connected to the battery,
wherein the charge control circuit outputs low to a third terminal of the switch circuit so that the first terminal of the switch circuit is electrically connected to the second terminal of the switch circuit when the battery is not overcharged,
wherein the charge control circuit outputs high to the third terminal of the switch circuit so that the first terminal of the switch circuit is not electrically connected to the second terminal of the switch circuit when the battery is overcharged, and
wherein the voltage of the battery is confirmed by transmitting the modulated signal through the antenna.

2. The device according to claim 1,
wherein the second circuit comprises an A/D conversion circuit, a clock generation circuit, and a logic circuit which are connected to each other.

3. A system comprising the device according to claim 1, an external antenna, and a transmitter.

4. The device according to claim 1, wherein a chassis of the cardiac pacemaker device is formed of a resin material.

5. The device according to claim 4, wherein the chassis is coated with a diamond-like-carbon film.

6. A cardiac pacemaker device comprising the device according to claim 1.

7. A device comprising:
an atrium detection amplifier circuit for detecting and amplifying an electrocardiogram of an atrium;
a chamber detection amplifier circuit for detecting and amplifying an electrocardiogram of a chamber;
a controller circuit for outputting an abnormal signal when an arrhythmia is detected into which amplification signals of the atrium detection amplifier circuit and the chamber detection amplifier circuit is inputted to measure the electrocardiograms and calculate a pulse cycle, as well;
a pulse generation circuit for outputting an electric pulse which stimulates a heart when the abnormal signal is inputted into the controller circuit;
a battery for supplying an electric power to the atrium detection amplifier circuit, the chamber detection amplifier circuit, the controller circuit, and the pulse generation circuit;
an internal antenna for receiving a wireless signal transmitted from an external device;
a rectifying and smoothing circuit for converting the wireless signal received by the internal antenna into direct current;
a charge circuit for generating current based on an electric power of the rectifying and smoothing circuit and charging the battery, the charge circuit comprising a constant current source and a switch circuit; and
a charge control circuit for monitoring the battery so as not to be charged too much, and for controlling the charge circuit and suppressing a charge amount of the battery when the charge amount of the battery is overcharged;
a residual amount detection circuit for monitoring a voltage of the battery and converting the voltage into a digital signal; and
a modulation circuit for modulating the digital signal, the modulation circuit being connected to the residual amount detection circuit,
wherein the modulated wireless signal is transmitted to the external device through the internal antenna,
wherein a first terminal of the switch circuit is electrically connected to the constant current source,
wherein a second terminal of the switch circuit is electrically connected to the battery,
wherein the charge control circuit outputs low to a third terminal of the switch circuit so that the first terminal of the switch circuit is electrically connected to the second terminal of the switch circuit when the battery is not overcharged,
wherein the charge control circuit outputs high to the third terminal of the switch circuit so that the first terminal of the switch circuit is not electrically connected to the second terminal of the switch circuit when the battery is overcharged, and
wherein the voltage of the battery is confirmed by transmitting the modulated signal through the antenna.

8. A system comprising the device according to claim 7, an external antenna, and a transmitter.

9. The device according to claim 7, wherein a chassis of the device is formed of a resin material.

10. The device according to claim 9, wherein the chassis is coated with a diamond-like-carbon film.

11. A cardiac pacemaker device comprising the device according to claim 7.

* * * * *

UNITED STATES PATENT AND TRADEMARK OFFICE
CERTIFICATE OF CORRECTION

PATENT NO.        : 8,838,244 B2                                    Page 1 of 1
APPLICATION NO.   : 11/798817
DATED             : September 16, 2014
INVENTOR(S)       : Jun Koyama It is certified that error appears in the above-identified patent and that said Letters Patent is hereby corrected as shown below:

In the Claims

In claim 4, at column 12, line 63, delete "cardiac pacemaker".

Signed and Sealed this
Tenth Day of February, 2015

Michelle K. Lee
*Deputy Director of the United States Patent and Trademark Office*